United States Patent
Mitchell et al.

(10) Patent No.: US 9,034,171 B2
(45) Date of Patent: May 19, 2015

(54) FUEL CELL FERMENTATION MONITOR

(71) Applicant: Alcotek, Inc., St. Louis, MO (US)

(72) Inventors: John Mitchell, Manchester, MO (US); Karl R. Wolf, Jr., Eureka, MO (US); Patrick Clifford, Florissant, MO (US)

(73) Assignee: Alcotek, Inc., St. Louis, MO (US)

( * ) Notice: Subject to any disclaimer, the term of this patent is extended or adjusted under 35 U.S.C. 154(b) by 0 days.

(21) Appl. No.: 14/201,433

(22) Filed: Mar. 7, 2014

(65) Prior Publication Data

US 2014/0251835 A1    Sep. 11, 2014

Related U.S. Application Data

(60) Provisional application No. 61/774,719, filed on Mar. 8, 2013.

(51) Int. Cl.
| | |
|---|---|
| *G01N 33/14* | (2006.01) |
| *C12G 1/00* | (2006.01) |
| *G01N 27/404* | (2006.01) |
| *G01N 33/497* | (2006.01) |

(52) U.S. Cl.
CPC .............. *G01N 33/146* (2013.01); *C12G 1/005* (2013.01); *G01N 27/4045* (2013.01); *G01N 2033/4977* (2013.01)

(58) Field of Classification Search
CPC ............ G01N 27/404; G01N 27/4045; G01N 33/0047
USPC .................................................. 204/431, 432
See application file for complete search history.

(56) References Cited

U.S. PATENT DOCUMENTS

| | | |
|---|---|---|
| 6,527,943 B1 | 3/2003 | Zhang et al. |
| 2002/0023849 A1 | 2/2002 | Vadgama et al. |

FOREIGN PATENT DOCUMENTS

| | | |
|---|---|---|
| JP | 2542604 B2 | 8/1988 |
| JP | 2801765 B2 | 6/1992 |
| WO | 2009006637 A2 | 1/2009 |

OTHER PUBLICATIONS

W. J. Criddle, et al. "On-line Determination of Ethanol During Fermentation Processes Using a Fuel Cell Sensor", Analyst, vol. 112, May 1987, p. 616-618.*
Palmer, John, "How to Brew, Chapter 8—Fermentation," http://www.howtobrew.com, 1999, 20 pages.
Palmer, John, "How to Brew, Chapter 9—Fermenting Your First Beer," http://www.howtobrew.com, 1999, 12 pages.
Palmer, John, "Appendix A—Using Hydrometers," http://www.howtobrew.com/appendices/AppendixA.html, 1999, 3 pages.
"Brewing," Wikipedia, http://en.wikipedia.org/wiki/Brewing, printed on Jul. 9, 2012, 18 pages.
"Ethanol Fermentation," Wikipedia, http://en.wikipedia.org/wiki/Ethanol_fermentation, printed on Jul. 9, 2012, 5 pages.
"Fermentation (wine)," Wikipedia, http://en.wikipedia.org/wiki/Fermentation_(wine), printed on Jul. 9, 2012, 5 pages.

(Continued)

*Primary Examiner* — J. Christopher Ball
(74) *Attorney, Agent, or Firm* — Lewis Rice LLC

(57) ABSTRACT

Systems and methods for implementing an automated process which calculates the current specific gravity of a liquid by using the original gravity of a fermenting liquid and a measurement of the percent alcohol by volume.

16 Claims, 7 Drawing Sheets

(56) References Cited

OTHER PUBLICATIONS

"Gravity (alcoholic beverage)," Wikipedia, http://en.wikipedia.org/wiki/Gravity_(alcoholic_beverage), printed on Jul. 9, 2012, 6 pages.

"Homebrewing—Measuring Alcohol Content of Your Beer," Drunkmansguide's Weblog, http://drunkmansguide.wordpress.com/2007/12/19/homebrewing . . . , printed on Jul. 9, 2012, 13 pages.

Manning, Martin P., "Understanding Specific Gravity and Extract," Brewing Techniques, Sep./Oct. 1993, 7 pages.

"Mid Infrared Sensors," Vital Sensors Technologies, World Brewing Congress, http://www.vitalsensorstech.com/PDF's/VitalSensors%20Presentation%20Testing%20ingredients%20at-%20Critical%20Process%20Points.pdf, Aug. 4, 2012, undated, 32 pages.

"Brewing Application Notes—On-Line Measurement of Plato Degree during Beer Fermentation Using Smar DT302 Density Transmitter," Smar, http://www.smar.com/PDFs/ApplicationNates/APPNOTESCE.pdf, Apr. 2011, 4 pages.

International Search Report, International Patent Application No. PCT/US2014/022043, issued on Jul. 18, 2014, 12 pages.

* cited by examiner

| Date | Time | Elapsed Days | Elapsed Minutes | Temperature (°F) | Hydrometer (Uncorrected) | Hydrometer (Corrected) | %ABV | Specific Gravity (derived from %ABV) |
|---|---|---|---|---|---|---|---|---|
| 11-AUG | 2:30 PM | 0.000 | 0 | 82 | 1.074 | 1.077 | | |
| 12-AUG | 2:15 PM | 0.990 | 1425 | 75 | 1.064 | 1.066 | | |
| 13-AUG | 7:00AM | 1.688 | 2430 | 73 | 1.048 | 1.050 | | |
| 13-AUG | 2:00 PM | 1.979 | 2850 | 74 | 1.044 | 1.046 | | |
| 14-AUG | 7:00 AM | 2.688 | 3870 | 74 | 1.040 | 1.042 | 4.7 | 1.042 |
| 15-AUG | 7:00 AM | 3.688 | 5310 | 73 | 1.034 | 1.035 | 5.2 | 1.038 |
| 15-AUG | 3:00 PM | 4.021 | 5790 | 73 | 1.034 | 1.035 | 5.9 | 1.033 |
| 21-AUG | 7:00 AM | 9.688 | 13950 | 72 | 1.025 | 1.026 | 6.5 | 1.028 |
| 22-AUG | 7:00 AM | 10.688 | 15390 | 72 | 1.022 | 1.023 | 7.6 | 1.020 |
| 26-AUG | 7:00 AM | 13.688 | 19710 | 72 | 1.020 | 1.021 | 7.3 | 1.022 |
| 27-AUG | 7:45 AM | 15.719 | 22635 | 72 | 1.018 | 1.019 | 8.1 | 1.016 |
| 29-AUG | 7:30 AM | 17.708 | 25500 | 72 | 1.016 | 1.017 | 8.1 | 1.016 |
| 3-SEP | 7:30 AM | 22.708 | 32700 | 72 | 1.014 | 1.015 | 8.4 | 1.014 |
| 10-SEP | 7:00 AM | 29.688 | 42750 | 72 | 1.011 | 1.012 | 8.5 | 1.013 |
| 15-SEP | 7:30 AM | 34.708 | 49980 | 73 | 1.009 | 1.010 | 8.9 | 1.010 |
| 20-SEP | 7:00 AM | 39.688 | 57150 | 73 | 1.007 | 1.008 | 9.1 | 1.009 |
| 22-SEP | 7:00 AM | 41.688 | 60030 | 72 | 1.007 | 1.008 | 9.2 | 1.008 |
| 24-SEP | 7:00 AM | 43.688 | 62910 | 72 | 1.006 | 1.007 | 9.5 | 1.006 |
| 26-SEP | 7:00 AM | 45.688 | 65790 | 72 | 1.005 | 1.006 | 9.3 | 1.007 |
| 28-SEP | 7:00 AM | 47.688 | 68670 | 73 | 1.005 | 1.006 | 9.5 | 1.006 |
| 30-SEP | 7:00 AM | 48.698 | 70125 | 73 | 1.005 | 1.006 | 9.6 | 1.005 |

Figure 4A

FUEL CELL FERMENTATION MONITOR

CROSS REFERENCE TO RELATED APPLICATION(S)

This application claims benefit of U.S. Provisional Patent Application No. 61/774,719 filed Mar. 8, 2013, the entire disclosure of which is incorporated herein by reference.

BACKGROUND

1. Field of the Invention

This disclosure is related to the field of devices and methods used to monitor fermentation. Specifically, this disclosure is related to devices and methods which are used to measure the percentage Alcohol By Volume (% ABV), specific gravity or sugar content of a fermented liquid.

2. Description of the Related Art

Fermentation is the process of live yeast cells acting on simple sugars dissolved in a liquid, producing ethanol, carbon dioxide gas, and trace amounts of other compounds. It is a process used in the making of beers, wines, and spirits by the chemical conversion of sugars into ethanol.

Certain alcoholic beverages, like beer and wine, are produced by fermenting sugars dissolved in water (called wort in beer, must in wine) using special strains of yeast. Brewers and wine makers generally monitor the progress of the fermentation process by measuring the fermenting beverage's specific gravity, or relative density compared to water, of the liquid at various stages in the fermentation process. Generally, a fermenting liquid's specific gravity is measured by manually taking small samples from the fermentor at periodic intervals and measuring the sugar content (in units called Brix, Plato, or Balling). Generally, wine makers traditionally use ° Brix, while brewers use ° Plato. ° Balling is the old unit used by brewers which has largely been replaced by ° Plato. Notably, all three units represent nearly the same values and can be used interchangeably.

Devices which are utilized in the art to take this manual measurement of a fermenting beverage's specific gravity include hydrometers, refractometers, pycnometers and oscillating U-tube electronic meters. A hydrometer, one of the devices most commonly utilized to measure the specific gravity of a liquid, generally works as follows. The hydrometer is a device of a generally constant weight that displaces different volumes of liquid as the liquid's density varies. Accordingly, the typical hydrometer consists of a weighted bulb with a slender graduated stem rising above it. Once the bulb is submerged, the increment of displacement with the depth is determined by the cross section of the stem, which is generally very small to ensure a high degree of accuracy.

The measured specific density of a fermenting liquid will be largely dependent on the sugar content of the fermenting liquid. During the fermentation process, yeast in the liquid converts sugars into carbon dioxide and alcohol. The decline in the sugar content of the liquid and the increase in the presence of ethanol (which is less dense than water) drop the density of the fermenting liquid—i.e., there is an inverse relationship between the specific gravity measurements and the amount of ethanol present in the fermenting liquid. The percentage of alcohol in the fermenting liquid can be calculated from the difference between the original specific gravity of the fermenting liquid and the current specific gravity of the fermenting liquid. By monitoring the decline in the specific gravity over time, the brewer obtains information on the health and progress of the fermentation and determines that it is complete when the gravity stops declining. When the fermentation is complete, the current specific gravity is then called the final gravity. Notably, when monitoring the progression of fermentation by specific gravity measurement, carbon dioxide bubbles may have to be drawn out of the liquid sample with a vacuum in order to get accurate specific gravity measurements. In certain instances, it might even be necessary to halt fermentation in the liquid sample in order to prevent continued carbon dioxide production.

From the measurement of specific gravity, ° Brix can be approximated as:

$$\text{Brix}=261.3\times(1-1/g), \qquad [\text{Eq. 1}]$$

where:

g is the specific gravity of the solution at 20° C.

As noted previously, during the course of the fermentation, the specific gravity value drops while the amount of ethanol rises; in fact, the relationship is almost linear and can be approximated as follows:

$$\%\text{ Alcohol by Volume}(\%\text{ ABV})=(O.G.-C.G.)\times 133.3, \qquad [\text{Eq. 2}]$$

where:

O.G. is the original specific gravity (before fermentation begins), and

C.C. is the current specific gravity.

When the fermentation is complete, the current gravity is called the final gravity and is designated F.G. In a typical pale ale, for example, the O.G. might be around 1.050 and the F.G. about 1.012; using Eq. 2 above, the % ABV of the finished beer would be approximately 5.1 percent.

There are several reasons why brewers and wine makers monitor the progress of their fermentations. The most common reason is to determine when the primary phase of the fermentation is complete (or nearly complete) and know when the product is ready to move to the next phase. Brewers typically transfer the beer from the fermentor to what is called a bright beer tank or lagering tank, where the beer is conditioned—and sometimes carbonated—for a time before it is packaged. Another reason to monitor specific gravity is to look out for any abnormalities—e.g., for a particular recipe using a healthy, standard yeast strain in a high quality wort, unless something is out of the ordinary, fermentation should progress in a well-behaved, repeatable fashion.

While it is the traditional methodology utilized in the fermented beverage industry, there are numerous problems with monitoring the progress of fermentations via manual specific gravity measurements. One major problem with the manual method of determining the specific gravity of a fluid is contamination. Every time you open the fermentors you are risking infection from airborne microbes. Once contamination reaches the fermenting liquid, the batch is generally ruined and must be discarded. Further, the current processes utilized in the art are manual, cumbersome, prone to human error, and often erratic and unreliable. Finally, due to their labor-intensive nature and the risk of infection, the currently utilized processes fail to adequately assess the progression of fermentation as the specific gravity measurements are only taken at intermittent periodic intervals. Stated differently, because the manual progress is so cumbersome and at-risk for contamination, only a few specific gravity measurements are taken during this fermentation process. This creates a very imprecise tool to measure the health and progression of the fermentation. Accordingly, if something unexpected happens during the fermentation (e.g., the yeast dies or is rendered ineffective), it is not often detected until it is too late to save the fermenting liquid.

SUMMARY

The following is a summary of the invention which should provide to the reader a basic understanding of some aspects of the invention. This summary is not intended to identify critical components of the invention, nor in any way to delineate the scope of the invention. The sole purpose of this summary is to present in simplified language some aspects of the invention as a prelude to the more detailed description presented below.

Because of these and other problems in the art, described herein is, among other things, a method for monitoring the fermentation process of a liquid, the method comprising: placing a liquid in a container having a headspace; and, with a fuel cell sensor, measuring a percentage alcohol content of one or more vapor samples taken from the headspace during fermentation of the liquid.

In an embodiment of the method described above, the liquid is selected from the group consisting of: wort and beer.

In another embodiment of the method described above, the liquid is selected from the group consisting of: must and wine.

In another embodiment of the method described above, the container comprises a fermentation vat.

In another embodiment of the method described above, the container comprises a sample container and the liquid comprises a sample of liquid which is simultaneously fermenting in a larger container.

Also described herein, among other things, is a method for monitoring the fermentation process of a liquid, the method comprising: placing a liquid in a container having a headspace; placing a fuel cell sensor in an antechamber, the antechamber being in vapor communication with the container; and, with the fuel cell sensor, measuring a percentage alcohol content of a vapor sample taken from the antechamber during fermentation of the liquid.

In an embodiment of the method described above, the antechamber is above the liquid.

In another embodiment of the method described above, the antechamber is within the liquid.

In another embodiment of the method described above, the liquid is selected from the group consisting of: wort and beer.

In another embodiment of the method, the liquid is selected from the group consisting of: must and wine.

In another embodiment of the method, the container comprises a fermentation vat.

In another embodiment of the method, the container comprises a sample container and the liquid comprises a sample of liquid which is simultaneously fermenting in a larger container.

In another embodiment of the method, the method further comprises: measuring a specific gravity of the liquid prior to placing the liquid in the container; and converting the percentage alcohol content to a specific gravity.

Also described herein, among other things, is a system for monitoring the fermentation process of a liquid, the system comprising: a fermentation vat, the fermentation vat being filled with a liquid and a headspace above the liquid; a sensor housing integral to the fermentation vat, the sensor housing defining an antechamber; a sampling mechanism; a sampling inlet; and a fuel cell sensor; wherein the concentration of alcohol in the antechamber is generally and proportionally the same as the concentration of alcohol in the liquid; wherein the sampling inlet connects the sampling mechanism to the antechamber; wherein the sampling mechanism connects the sampling inlet to the fuel cell sensor, the sampling mechanism taking at least one fixed sample from the antechamber on demand through the sample inlet; and, wherein the fuel cell sensor determines the percentage of alcohol in each fixed sample.

In an embodiment of the system, the sensor housing is positioned integral to the fermentation vat underneath the liquid in the fermentation vat.

In an embodiment of the system, the sensor housing is located positioned integral to the fermentation vat in the vat headspace.

In an embodiment of the system, the antechamber is separated from the vat headspace by at least one membrane.

In an embodiment of the system, at least one of the at least one membrane is a coarse foam guard screen.

In an embodiment of the system, at least one of the at least one membrane is a permeable membrane foam barrier.

In an embodiment of the system, at least one of the at least one membranes is a bacterial membrane.

BRIEF DESCRIPTION OF THE DRAWINGS

FIGS. 4A and 4B provide an embodiment of the plotted fermentation process over time produced from the readings obtained by the fuel cell fermentation monitor compared to readings from a conventional hydrometer.

DESCRIPTION OF THE PREFERRED EMBODIMENT(S)

Figure 1:
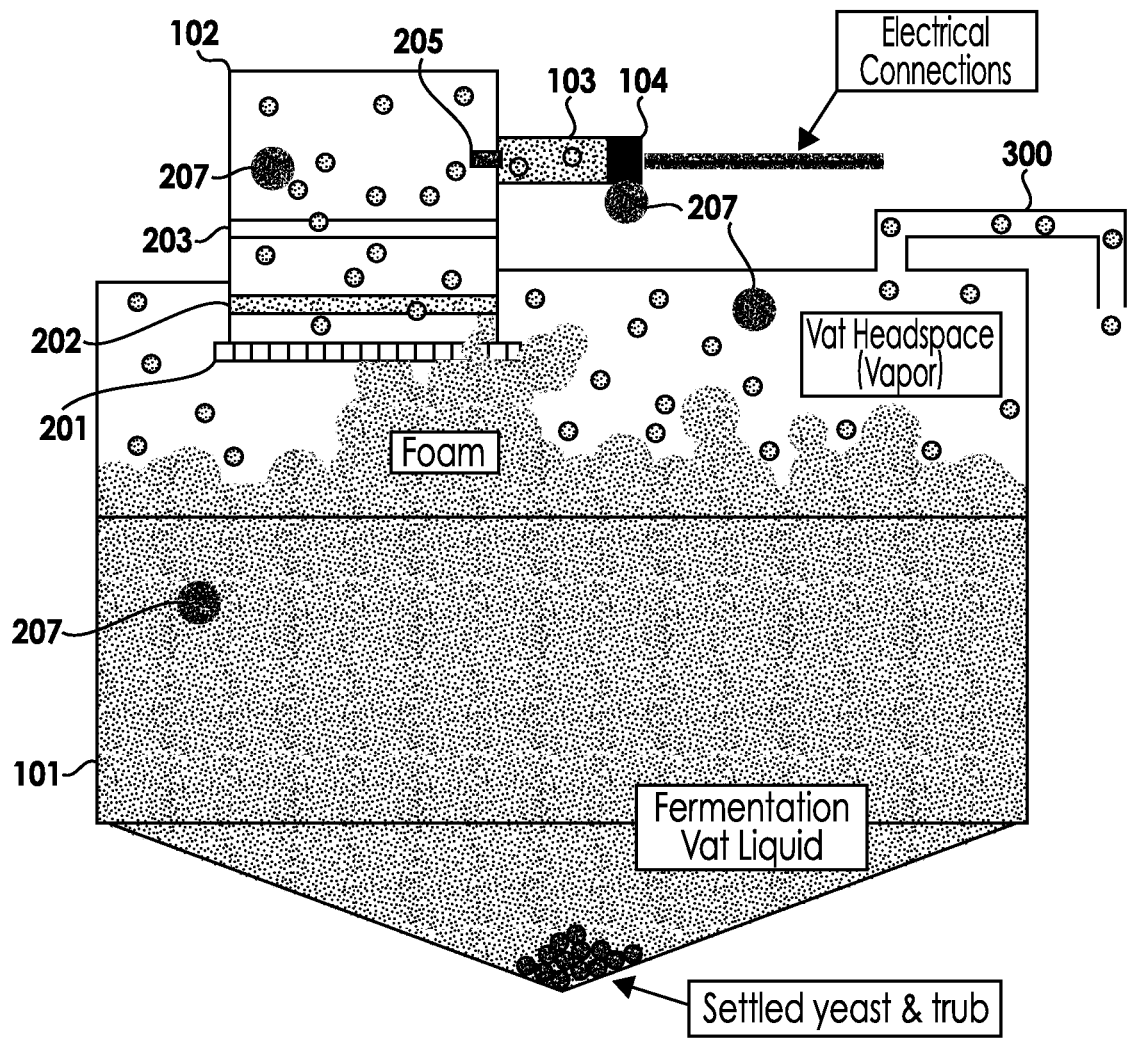
FIG. 1 provides a front cut-through view of an embodiment of the fuel cell fermentation monitor.

The following detailed description and disclosure illustrates by way of example and not by way of limitation. This description will clearly enable one skilled in the art to make and use the disclosed systems and apparatus, and describes several embodiments, adaptations, variations, alternatives and uses of the disclosed systems and apparatus. As various changes could be made in the above constructions without departing from the scope of the disclosures, it is intended that all matter contained in the above description or shown in the accompanying drawings shall be interpreted as illustrative and not in a limiting sense.

Described herein, among other things, is an automated process for calculating changes in the specific gravity of a fermenting liquid based upon changes in measured alcohol concentrations. In certain embodiments, this process allows for the fermentation progress to be consistently monitored using electronically measured alcohol concentrations rather than using the traditional manual specific gravity measurements.

Generally, the automated process disclosed herein utilizes the original gravity of a fermenting liquid and a measurement of the percent alcohol by volume (% ABV) to calculate the current specific gravity of a fermenting liquid. In each of the various embodiments disclosed herein, the % ABV is measured, as will be understood by one skilled in the art, through taking a sample of the gas in the headspace of the fermenting liquid or alternatively in the liquid itself, (for example, in a fermentation vat or in a liquid sample) and analyzing it with a fuel cell. The resulting % ABV output from the fuel cell is generally proportional to the amount of alcohol in the fermenting liquid. The periodic % ABV measurements obtained from the fuel cell are then used with the originally determined specific gravity of the liquid prior to fermentation to ascertain the progression and development of the fermentation over time.

FIGS. 1-3 and 5 provide front cut-through views of various embodiments of the disclosed fuel cell fermentation monitor and the methods, processes, devices and apparatuses associated therewith. In each of these embodiments, there is a fermentation vat (101), a sensor housing (102), a sampling mechanism (103) and a fuel cell sensor (104).

Generally, it should be understood that the fermentation vat (101) disclosed herein can include any fermentation vessel known to those of ordinary skill in the art including, but not limited to, stainless steel vats, wooden vats, wine barrels, carboys, plastic vessels and other fermentation vats known or utilized by those of ordinary skill in the art. Generally, when in use (e.g., as demonstrated in FIG. 1), the fermentation vat (101) will be partially filled with a certain amount of fermenting liquid creating a large volume of headspace above, and in equilibrium with, the fermenting liquid. Those skilled in the art will understand that the unit of weight of ethanol per volume of fermenting liquid will be thousands of times more concentrated than the equivalent unit volume of headspace gas. As demonstrated in FIG. 1, this vat headspace will hold the vapor emitted by the fermentation vat liquid. In certain embodiments, as depicted in FIGS. 1-3 and 5, a vent (300) integral to the fermentation vessel (101) and, in particular, the vat headspace will allow for the release of vapors from the fermentation vat due to pressure built up in the vat as a result of fermentation.

Integral to the fermentation vat (101) in each of the embodiments depicted in FIGS. 1-3 and 5 is the sensor housing (102). Notably, the shape, dimensions, internal volume, location and material composition of the sensor housing (102) is not determinative. Generally, it should be understood that the sensor housing (102) includes any housing apparatus known to those of ordinary skill in the art that is integral to the fermentation vat (101), can house the sampling inlet (205) (or a combination of the sampling inlet (205), sampling mechanism (103), or fuel cell sensor (104)), and can create a space for the movement of the vapor of the fermenting liquid from the fermentation vat (101) to the sensor housing (102). Depending on the embodiment, the sensor housing (102) will be positioned integral to the vat headspace or, in other embodiments (see, e.g., FIG. 5), the sensor housing (102) will be positioned integral to the fermentation vat (101) underneath the fermentation liquid level.

Those skilled in the art will understand that the sensor cannot reasonably be placed directly in the vat headspace since foam and scum will interfere with accurate sampling and measurement, certainly during active fermentation. Thus, an antechamber is created as part of the sensor housing to create, in a sense, a portion of vat headspace wherein foam and scum cannot enter in any appreciable or problematic amount. This is true of any number of sensor types that might be used to measure the ethanol in the headspace such as, but not limited to, infrared sensors, Raman sensors, or the extracting of gas samples for gas chromatographs. Sensor type is not meant to limit the scope of the invention.

Figure 2:
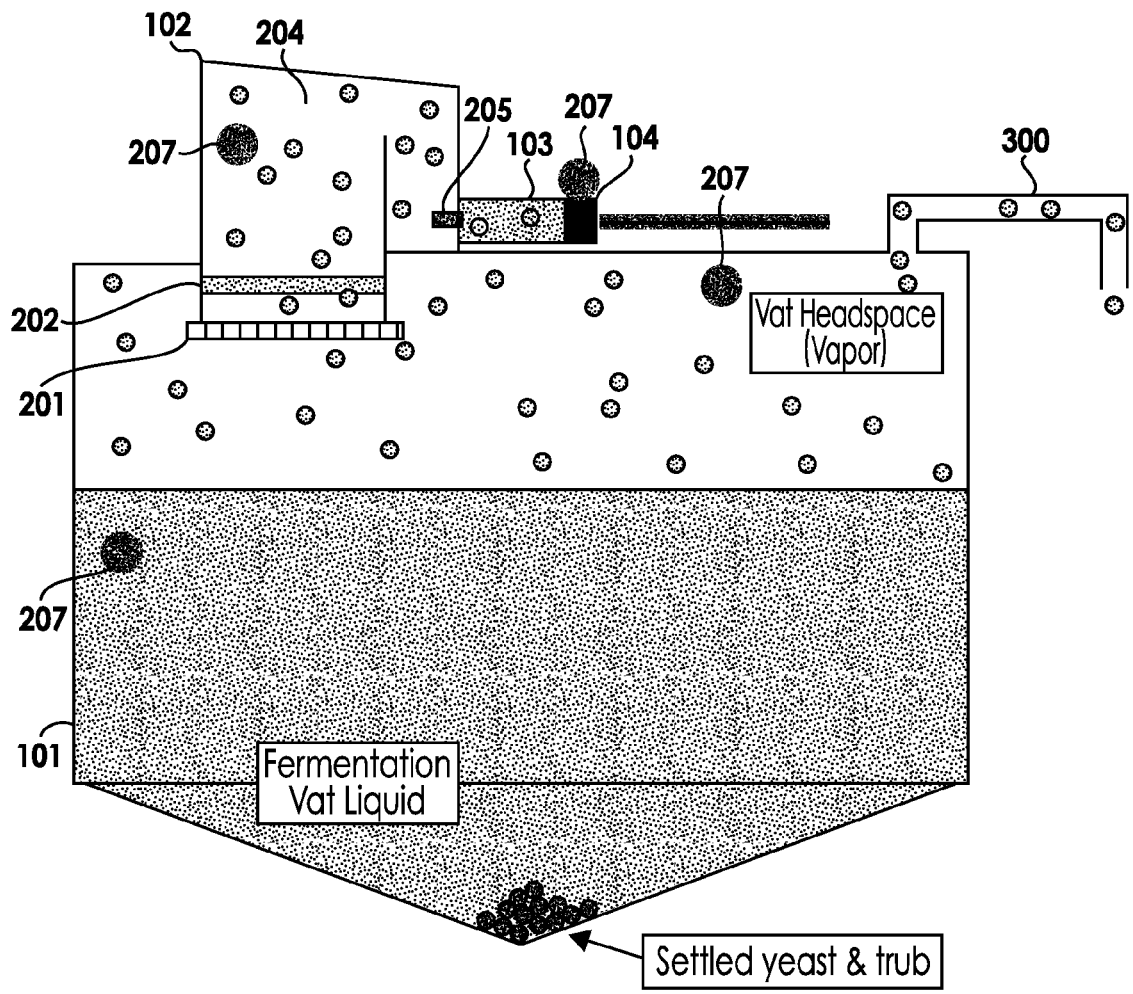
FIG. 2 provides a front cut-through view of another embodiment of the fuel cell fermentation monitor.
Figure 3:
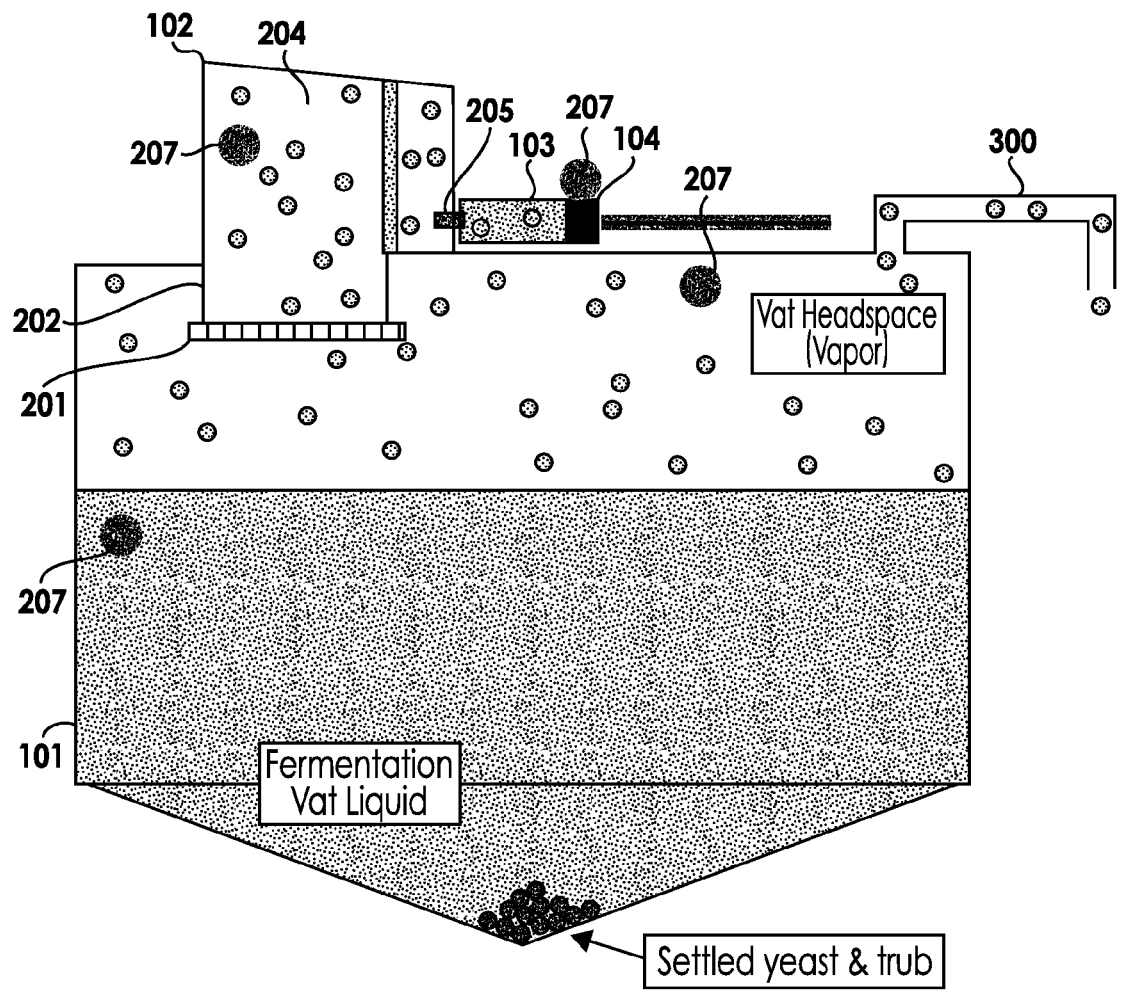
FIG. 3 provides a front cut-through view of yet another embodiment of the fuel cell fermentation monitor.
Figure 5:
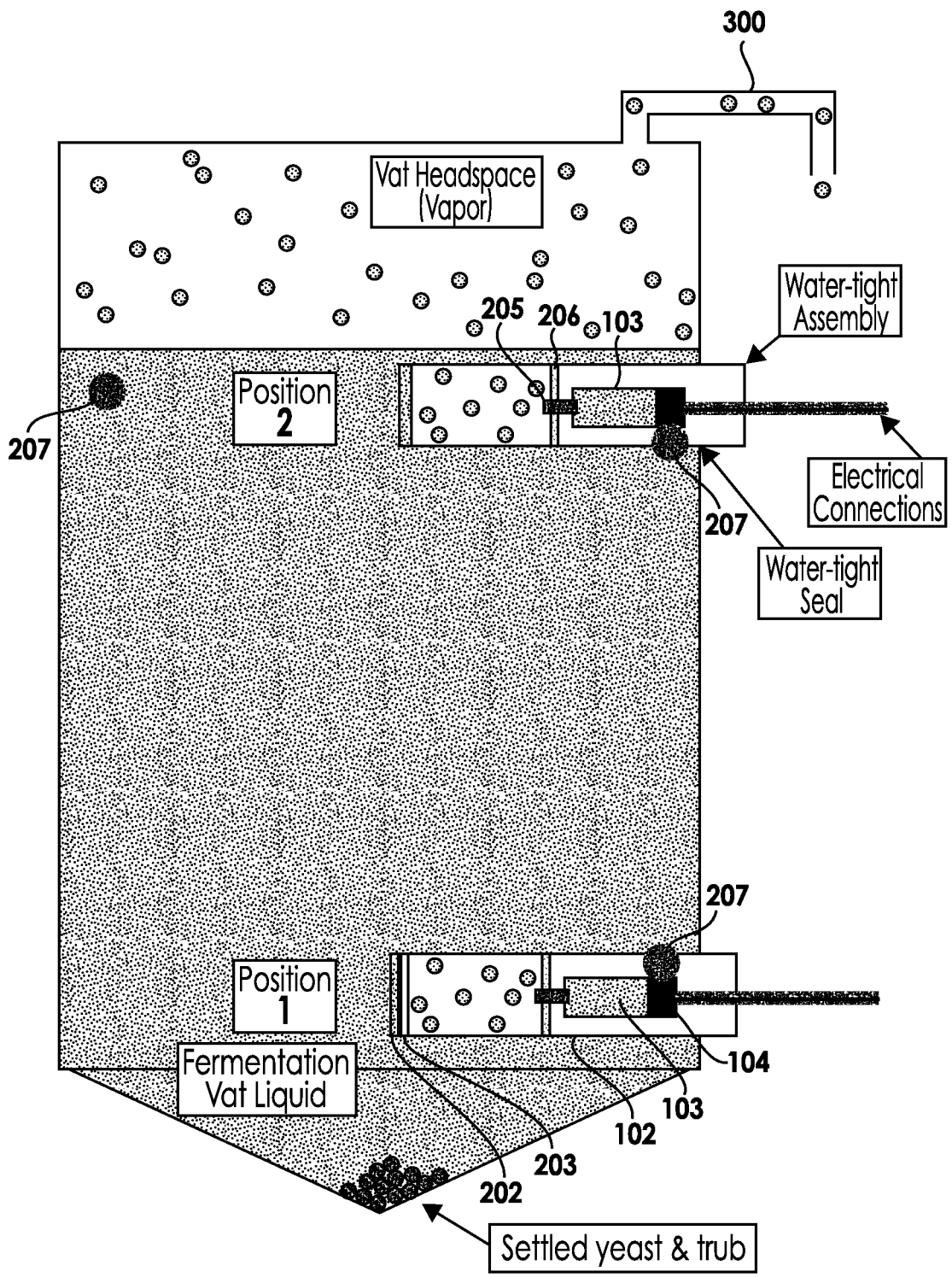
FIG. 5 provides a front cut-through view of yet another embodiment of the fuel cell fermentation monitor.

In an embodiment of the disclosed fuel cell fermentation monitor methods, systems, processes, devices and apparatuses associated therewith, as touched upon previously, the sensor housing (102) defines a small volume, or an antechamber. In certain embodiments, as depicted in FIGS. 1-3, the antechamber defined by the sensor housing (102) is in communication with the large volume of vat headspace above the liquid that partially fills the fermentation vat (101). Generally, being integrally connected and in equilibrium, the concentration of alcohol in the vat headspace is generally the same as the concentration of alcohol in the sensor housing antechamber provided both the vat headspace and the sensor housing antechamber are generally at the same temperature. In another embodiment, as depicted in FIG. 5 and discussed further herein, the antechamber defined by the sensor housing (102) is in communication with the liquid that fills the fermentation vat.

In certain embodiments, it is desirable that the sampling mechanism (103) and the fuel cell sensor (104) only sample from the antechamber because the vapors in this volume are generally clean and devoid of any liquids or solids in the sample. In these embodiments, it is contemplated that the antechamber is separated from the vat headspace or the fermenting liquid (depending on the embodiment) by one or more screens or membranes.

For example, in certain other embodiments, as depicted in FIGS. 1-3, the antechamber is separated from the vat headspace by a coarse foam guard screen (201). This coarse foam guard screen (201) generally functions as a first barrier against foam or other large particles entering the antechamber. Generally, any screen or membrane mechanism known to those of ordinary skill in the art that is able to filter out foam or other large particles while allowing vapors, such as alcohol vapors, to enter into the antechamber is contemplated in this application. In addition, in certain embodiments such as those depicted in FIGS. 1-3, the antechamber is further separated from the vat headspace volume by a gas permeable foam guard membrane (202) that stops liquid, but allows vapors, such as alcohol vapors, to pass therethrough. In the embodiments disclosed in FIG. 3, the gas permeable membrane foam barrier (202) completely separates the portion of the antechamber where the sampling inlet is located from the portion of the antechamber which is in fluid communication with the vat headspace of the fermentation vat (101).

Further, as demonstrated in FIGS. 1 and 2, it is contemplated that the alcohol vapors in the antechamber which are in fluid communication with the sampling inlet (205) and sampling mechanism (103) will be further separated from the vat headspace by a bacterial membrane (203) known to those of ordinary skill in the art. Generally, this bacterial membrane (203) will function to prevent any bacteria that might be in the sensor, sampling system, or sensor antechamber from entering the fermentation vat (101), including its headspace. As noted previously, depending on the embodiment, this bacterial barrier (203) can be formed by a gas permeable bacteria barrier known to those of ordinary skill in the art or, in alternative embodiments, by the shape of the sensor housing (e.g., forming a "swan's neck" as depicted in FIG. 2). In certain embodiments, it is contemplated that both mechanisms will be utilized. In addition, in alternative embodiments it is contemplated that the antechamber sensor housing (202) may be comprised of copper or brass or other known material that inhibits bacterial growth. Further, any barrier technology known to those of ordinary skill in the art for blocking bacteria from entering a vapor headspace and/or the fermenting liquid is contemplated in this application. In an embodiment, a gas permeable membrane and a bacterial barrier comprise the same element.

In general, the sampling mechanism (103) of the device of FIGS. 1-3 and 5 connects the fuel cell sensor (104) to the sensor housing antechamber (102) and acts as a conduit for the vapor from the sensor housing antechamber (102) to the fuel cell sensor (104). In certain embodiments, the sampling mechanism (103) is generally comprised of a sampling inlet (205) and a sampling mechanism (103) known to those of ordinary skill in the art. Generally, any sampling inlet and sampling mechanism methodology known to those of ordinary skill in the art for use with a fuel cell sensor is contemplated in this disclosure, including sampling by diffusion. The sampling inlet (205) generally functions to connect the sampling mechanism (103) and the sensor housing (102) volume—i.e., it connects the fermenting vapor to the sampling mechanism (103). In general, the sampling mechanism (103), which in certain embodiments is an electromechanical sampling mechanism (103), takes samples (in certain embodiments, very small samples) from the antechamber on demand through the sample inlet (205) which is integral to the antechamber. In one embodiment, the electromechanical sampling mechanism will take samples on the order of microliters. Notably any sampling mechanism (103) known to those of ordinary skill in the art is contemplated in this application, including the use of apertures and/or diffusion. Check valves may or may not be used in the sampling mechanism.

Figure 6:
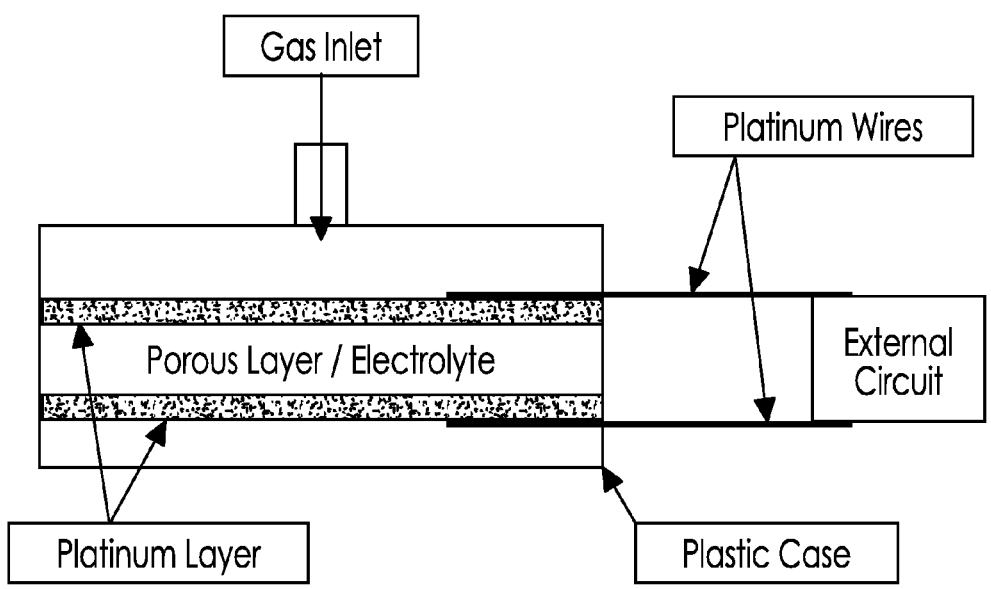
FIG. 6 depicts a basic configuration of a fuel cell sensor and assembly.

The fuel cell sensor (104) of the fuel cell fermentation monitor disclosed herein generally functions by taking a small fixed volume of vapor into the fuel cell sensor (104) from the sampling mechanism (103). An embodiment of one such fuel cell sensor (104) is provided in FIG. 6. The alcohol is then burned or otherwise reacted in the fuel cell sensor (104) and a certain number of electrons are produced for each molecule of alcohol vapor burned or reacted. These electrons are counted by an external circuit and a measurement representing the % ABV in the sample is produced. By always taking a fixed volume sample, the test is standardized—e.g., when the air space sample contains twice the concentration of alcohol compared to another sample, twice the electrons are produced and the measurement is twice as large. Comparably, if the sampling method is diffusion, fixed time may be used in a similar manner, instead of fixed volume.

It should be understood that any fuel cell sensor known to those of ordinary skill in the art that is able to calculate the % ABV of a vapor sample is contemplated in this application, including, but not limited to, continuous exposure fuel sensors, continuous exposure semiconductor sensors, infrared sensors aimed across or into the antechamber, and raman sensors aimed across or into the antechamber. In addition, it should be understood that other mechanisms known to those of ordinary skill in the art for calculating the % ABV of a vapor sample, such as but not limited to infrared sensors, are also contemplated within the scope of the fuel cell sensors discussed herein.

In certain embodiments, it is contemplated that the fuel cell sensor (104) will have to be calibrated prior to use. One contemplated method for calibrating the fuel cell sensor (104) is as follows. In a first step, a known % ABV solution is created using ethanol and water. Then the solution is placed in a jar or other device (e.g., the fermentation vat), which allows for headspace. Next, the jar, liquid and headspace are heated to a known constant temperature and allowed to equilibrate, as will be understood by those skilled in the art. In a final step, the headspace gas is sampled into a fermentation sampling system/fuel cell. Then the result output of the fuel cell sensor (104) is calibrated to the known % ABV of the solution; e.g., 5.00%.

An alternative embodiment of the fuel cell fermentation monitor is provided in FIG. 5. A problem that can occur with certain constructions of the cell fermentation monitor is the ability to keep foam and other debris that might be lifted up by the foam away from the fuel cell sensor (104). Foam can interfere with the function of the gas permeable foam guard membrane (202) over the course of fermentation. Further, if the foam were to breach into the antechamber, it could interfere with the operation and/or accuracy of the fuel cell sensor over the course of fermentation. In addition to the foam, the construction of the fuel cell fermentation monitor must incorporate safeguards against unsanitary items being dropped into the biological sanctity of the fermentation vat, thereby adversely impacting the sterilization of the fermentation. To combat these potential problems, in the alternative embodiment of the fuel cell fermentation monitor provided in FIG. 5, the fuel cell sensor (104), the sampling mechanism (103) and the sensor housing (102) are located within the liquid, such as at the bottom, of the fermentation vat (101). This orientation lessens the probability of foam interference with the process and places the sampling mechanism (103) and fuel cell sensor (104) in a location more amenable to maintenance or use from an operational viewpoint. Further, temperature issues become much less of a problem in this orientation where the sensor housing (102) protrudes into the fermentation vat (101).

As demonstrated more fully in FIG. 5, in this embodiment the sensor housing (102), sampling mechanism (103), and fuel cell sensor (104) are located in the fermentation vat at a location where the sensor housing (102) will be covered by fluid. As demonstrated in FIG. 5, it is contemplated that the sensor housing (102), sampling mechanism (103) and fuel cell sensor (104) may be located at or near the bottom of the fermentation vat (101)—position 1, at or near the top of the fermenting liquid—position 2, or at a plurality of other positions in the fermentation vat (101) wherein the sensor housing (102), sampling mechanism (103) and fuel cell sensor (104) are submerged in the fermenting liquid in the fermentation vat (101). Generally, the pressure on the antechamber gas space and the sensor sample chamber is proportionally related to the height of the liquid above the sensor housing in the fermentation vat (101). Accordingly, a position of the sensor housing (102) in the fermenting liquid can be chosen in accordance with the amount of pressure desired to be exerted on the fuel cell sensor (104) and the sensor housing (102) (e.g., position 2 might be chosen for the sensor assembly in order to minimize pressure issues). In an embodiment, multiple sensors in multiple positions may be used to provide for multiple points of reference. In another embodiment, other design accommodations or decisions may be made, including but not necessarily limited to varying or different membrane porosity, depending upon pressure issues.

In this embodiment, as depicted in FIG. 5, the sensor housing (102) encapsulates the fuel cell sensor (104), the sampling mechanism (103) and a space defining an antechamber. In general, as seen in FIG. 5, the interior volume of the sensor housing (102) is separated from the fermenting fluid by a series of membranes or barriers known to those of ordinary skill in the art. For example, in an embodiment, the antechamber is separated from the fermenting liquid by a liquid barrier (202) (such as a gas permeable membrane known to those of ordinary skill in the art) and a bacteria barrier (203) (such as a gas permeable membrane known to those of ordinary skill in the art). In alternative embodiments, it is further recognized that the fuel cell sensor (104) and the sampling mechanism (103) may be separated from the antechamber by a rigid or flexible air-tight membrane (not shown) known to those of ordinary skill in the art.

Generally the mechanisms and devices disclosed herein, embodiments of which are depicted in FIGS. 1-3 and 5, are designed such that any momentary drop in pressure in the antechamber that may occur when the sampling mechanism is activated is quickly re-equalized due to the gas permeable membranes located in the sensor housing (102) and, in certain embodiments, in the vat headspace (101). In certain embodiments, this pressure drop is minimized by virtue of the large volume antechamber compared to the smaller sampling mechanism/fuel cell volume. Generally, the bigger the pores in the membrane, the quicker the equalization will occur.

In other embodiments of the devices and mechanisms disclosed herein, one or more temperature sensors (207) will be incorporated into various elements of the system, e.g., in the fermentation vat (101), in the sensor housing (102), and in the sampling mechanism (103). FIGS. 1-3 and 5 depict embodiments of the devices and mechanisms disclosed herein with temperature sensors located at various points throughout the device. In other embodiments, it is contemplated that the devices and mechanisms disclosed herein will further comprise heating mechanisms known to those of ordinary skill in the art. It is generally contemplated that these heating mechanisms can be activated and heated to minimize condensation in the devices and mechanisms disclosed herein.

In any of these embodiments, there could be design elements of the antechamber, membranes, sensor and sampling mechanism that facilitate "clean-in-place," i.e., automatic cleaning systems used in breweries and elsewhere for sanitation of the equipment between batches. Such designs would allow typical clean-in-place procedures to be used without removing elements of the measuring system during the cleaning, and avoiding temporary or permanent damage to the measuring system as a result of the cleaning process.

In certain embodiments, the methods and processes for monitoring a fermenting liquid via a fuel cell sensor disclosed herein will proceed as follows. In a first step, an initial specific gravity reading is taken of the fermenting liquid (i.e., a specific gravity measurement of the liquid before the yeast is added thereto). This initial reading can be taken manually or automatically through any mechanism known to those of ordinary skill in the art for taking an original specific gravity measurement of a fluid. For example, in an embodiment, it is contemplated that this initial specific gravity reading will be taken with a hydrometer. In a second step, the sampling mechanism (103) and the fuel cell sensor (104) (which is independently calibrated to read in % ABV) take in and analyze a vapor sample from the antechamber at pre-programmed intervals. In an embodiment, the sampling mechanism (103) and the fuel cell sensor (104) take in and analyze a vapor sample from the antechamber only once.

Figure 4B:
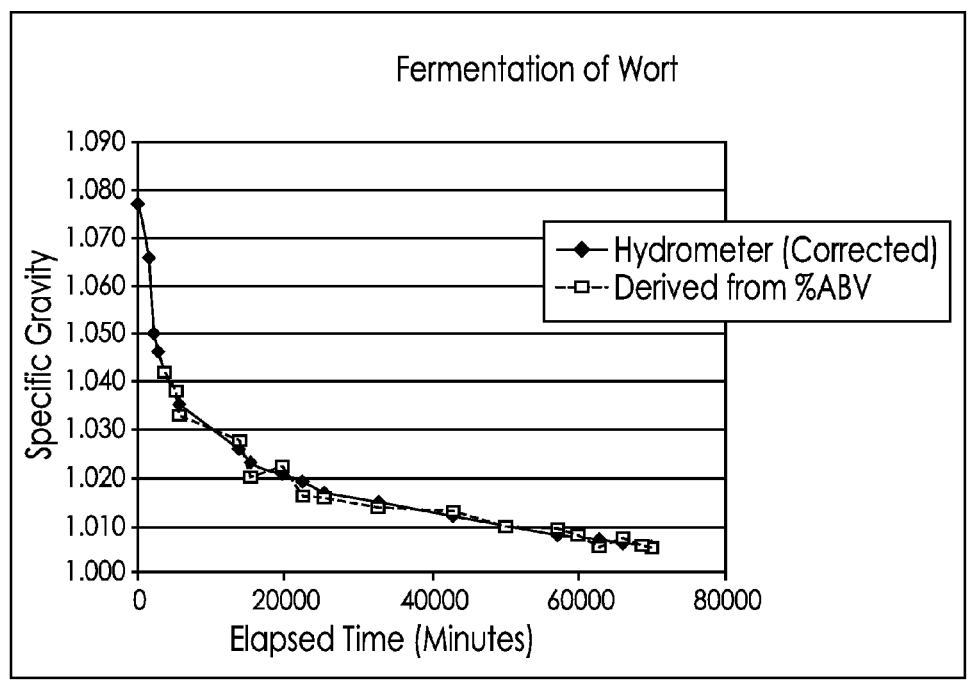

For example, in one embodiment, the sampling mechanism and fuel cell sensor (104) will take in and analyze a vapor sample from the antechamber every half an hour for a two week period. In another embodiment, a vapor sample will be taken from the headspace above the fermenting liquid and analyzed about every fifteen minutes for the duration of the fermentation process. In a still further embodiment, a reading may be taken near continuously to allow for near real-time measurements. In a third step, once the readings are obtained, the readings are plotted, usually in specific gravity, against time, presenting a picture of the fermentation process and also depicting stalls in the process towards completion. This creates a visual picture of the progress of the fermentation process over time, depicting stalls in the fermentation process as well as completion. Accordingly, this allows an operator or administrator to monitor the fermentation process in virtually real-time conditions. One embodiment of this plotted fermentation process is provided in FIG. 4. In a fourth step, the current gravity of the fermenting solution is determined by using the following equation:

$$C.G. = O.G. - (\% ABV/133.3)$$

In certain embodiments of this process, it is contemplated that the fuel cell sensor (104) will be connected to a computer, series of computers, network or other interface known to those of ordinary skill in the art either by wire or wirelessly. In these embodiments, it is contemplated that the computer, network or interface offers a display of the information related to the progress of the fermentation, as well as information regarding the storage and recalls of previous fermentations (whether in this vat, by this user, or by others in other locations). Such a computer could be programmed to detect deviations from an expected fermentation process and notify a user of such deviation as it is detected. Similarly, if a deviation is detected, the computer could decrease the time between taking samples to determine if the deviation indicates a particular condition.

In other embodiments, it is contemplated that the method and processes for monitoring a fermenting liquid via a fuel cell sensor (104) disclosed herein will be applied to a small, drawn liquid sample from the fermentation vat (or other non-fermentation vat or applicable container known to those of ordinary skill in the art) and take a snapshot in time by putting the sample in a mini-container with a lid and creating a condition similar to a vat—i.e., a liquid in equilibrium with a headspace gas. This allows for the fuel cell mechanism to be used to test samples that are removed from the fermentation vat for other reasons, such as tasting or to verify hydrometer readings. Next, the gas in the mini-container is directly sampled with a fuel cell sensor (104) to get an alcohol concentration of the liquid. It is contemplated that the container could be heated to a specific temperature or could record room temperature or that the sample could otherwise be manipulated to enhance the reading.

It should be noted that the methods and processes disclosed herein are not limited to brewing operations and can be applied to any situation where it would be desirable to monitor the change in the % ABV of a liquid over time or in the total ABV of a liquid system, e.g., in pumped breast milk. In cases where the system is used to measure total ABV of a liquid at some point in time, it is contemplated that the calibration of the measurement system may need to be adjusted depending on the nature of the liquid being measured. Such adjustments may be built into the measuring system or may be a result of exactly how the calibration process is carried out. This adjustment is due to different liquids partitioning with the headspace in different ratios. For example, the headspace over the same volume of breast milk and light beer might measure to be the same concentration at some point in time, at the same temperature, but the gas concentration may translate to 5.1% concentration of alcohol in the liquid (v/v) in one case and 4.7% in the other. In any embodiment that does not control the liquid/headspace container at a certain temperature, calibration may need to be adjusted depending on the exact temperature.

The advantages of the automated disclosed devices, systems, methods and processes for measuring the percentage of ABV, or measuring the percentage of ABV and, thus, the specific gravity of a fermenting liquid, are numerous. For example, because a manual sample is no longer needed or required, the progress of the fermentation can be monitored and analyzed automatically in real time, freeing the brewer or technician to perform other tasks (or to allow a less skilled employee to monitor the fermentation). In addition, the efficacy of the measurements is increased since the measurements can be taken at a much higher rate, thereby providing better insight into determining the quality of the fermentation and knowledge of when the product is ready for transfer. Finally, as the tests can be performed without opening the fermentation vessel, the likelihood of contamination is decreased.

While the invention has been disclosed in conjunction with a description of certain embodiments, including those that are currently believed to be the preferred embodiments, the detailed description is intended to be illustrative and should not be understood to limit the scope of the present disclosure. As would be understood by one of ordinary skill in the art, embodiments other than those described in detail herein are encompassed by the present invention. Modifications and variations of the described embodiments may be made without departing from the spirit and scope of the invention.

The invention claimed is:

1. A method for monitoring the fermentation process of a liquid, the method comprising:
    placing a liquid in a container having a headspace;
    placing a fuel cell sensor in an antechamber, the antechamber being in vapor communication with the container and within the liquid; and
    with the fuel cell sensor, measuring a percentage alcohol content of a vapor sample taken from the antechamber during fermentation of the liquid.

2. The method of claim 1 wherein said liquid is selected from the group consisting of: wort and beer.

3. The method of claim 1 wherein said liquid is selected from the group consisting of: must and wine.

4. The method of claim 1 wherein said container comprises a fermentation vat.

5. The method of claim 1 wherein said container comprises a sample container and said liquid comprises a sample of liquid which is simultaneously fermenting in a larger container.

6. A method for monitoring the fermentation process of a liquid, the method comprising:
    measuring a specific gravity of a liquid prior to placing the liquid in a container having a headspace;
    placing the liquid in the container;
    placing a fuel cell sensor in an antechamber, the antechamber being in vapor communication with the container; and
    with the fuel cell sensor, measuring a percentage alcohol content of a vapor sample taken from the antechamber during fermentation of the liquid; and
    converting the percentage alcohol content to a specific gravity.

7. A system for monitoring the fermentation process of a liquid, the system comprising:
    a fermentation vat, the fermentation vat being filled with a liquid and a headspace above the liquid;
    a sensor housing integral to the fermentation vat, the sensor housing defining an antechamber;
    a sampling means;
    a sampling inlet; and
    a fuel cell sensor;
    wherein the concentration of alcohol in the antechamber is generally and proportionally the same as the concentration of alcohol in the liquid;
    wherein the sampling inlet connects the sampling mechanism to the antechamber;
    wherein the sampling means connects the sampling inlet to the fuel cell sensor, the sampling means taking at least one fixed sample from the antechamber on demand through the sample inlet;
    wherein the fuel cell sensor determines the percentage of alcohol in each of the at least one fixed sample; and
    wherein the sensor housing is positioned integral to the fermentation vat underneath the liquid in the fermentation vat.

8. The system of claim 7 wherein said liquid is selected from the group consisting of: wort, beer, must, and wine.

9. The method of claim 6 wherein the antechamber is above the liquid.

10. The method of claim 6 wherein the antechamber is within the liquid.

11. The method of claim 6 wherein said liquid is selected from the group consisting of: wort, beer, must, and wine.

12. The method of claim 6 wherein said container comprises a fermentation vat.

13. The method of claim 6 wherein said container comprises a sample container and said liquid comprises a sample of liquid which is simultaneously fermenting in a larger container.

14. A system for monitoring the fermentation process of a liquid, the system comprising:
    a fermentation vat, the fermentation vat being filled with a liquid and a headspace above the liquid;
    a sensor housing integral to the fermentation vat, the sensor housing defining an antechamber;
    a sampling means;
    a sampling inlet; and
    a fuel cell sensor;
    wherein the concentration of alcohol in the antechamber is generally and proportionally the same as the concentration of alcohol in the liquid;
    wherein the sampling inlet connects the sampling mechanism to the antechamber;
    wherein the sampling means connects the sampling inlet to the fuel cell sensor, the sampling means taking at least one fixed sample from the antechamber on demand through the sample inlet;
    wherein the fuel cell sensor determines the percentage of alcohol in each of the at least one fixed sample; and
    wherein the antechamber is separated from the vat headspace by at least one membrane, said at least one of said at least one membrane being a course foam guard screen, a permeable membrane foam barrier, or a bacterial membrane.

15. The system of claim 14, wherein the sensor housing is located positioned integral to the fermentation vat in the vat headspace.

16. The system of claim 14 wherein said liquid is selected from the group consisting of: wort, beer, must, and wine.

* * * * *